US008177084B2

(12) United States Patent
Fox et al.

(10) Patent No.: US 8,177,084 B2

(45) Date of Patent: May 15, 2012

(54) CONTAINER ASSEMBLY AND PRESSURE-RESPONSIVE PENETRABLE CAP FOR THE SAME

(75) Inventors: William A. Fox, Burlington, NC (US); Charles Leo Carrico, Jr., Burlington, NC (US)

(73) Assignee: TriPath Imaging, Inc., Burlington, NC (US)

( * ) Notice: Subject to any disclaimer, the term of this patent is extended or adjusted under 35 U.S.C. 154(b) by 1572 days.

(21) Appl. No.: 11/353,482

(22) Filed: Feb. 13, 2006

(65) Prior Publication Data

US 2007/0187353 A1 Aug. 16, 2007

(51) Int. Cl.

*B65D 41/00* (2006.01)
*B65D 51/00* (2006.01)
*B01L 99/00* (2010.01)
*A61B 19/00* (2006.01)

(52) U.S. Cl. ......... 215/354; 215/247; 422/570; 604/415

(58) Field of Classification Search .................. 215/354, 215/343, 344, 247, 329; 604/415; 422/568, 422/570

See application file for complete search history.

(56) References Cited

U.S. PATENT DOCUMENTS

D3,806 S 12/1869 Shaffer
D24,337 S 5/1895 Gilchrist
686,642 A 11/1901 Wayte
769,021 A 8/1904 Risse
2,526,622 A 10/1950 Martin
3,080,993 A * 3/1963 Livingstone .................. 220/305
3,143,235 A 8/1964 Lowen
3,343,700 A 9/1967 Heubl
3,460,702 A 8/1969 Andrews
3,607,098 A 9/1971 Strande
3,653,528 A 4/1972 Wimmer
3,696,955 A 10/1972 Kundt et al.
3,944,104 A * 3/1976 Watson et al. ................ 215/307
3,957,653 A 5/1976 Blecher
3,986,627 A 10/1976 Zapp (Continued)

FOREIGN PATENT DOCUMENTS

EP 0 642 983 A1 3/1995

(Continued)

OTHER PUBLICATIONS

Office Action for Japanese Application No. 2008-554545 dated Mar. 27, 2012.

*Primary Examiner* — Robin Hylton

(74) *Attorney, Agent, or Firm* — Alston & Bird LLP

(57) ABSTRACT

A pressure-responsive container assembly and elastically-deformable penetrable cap is provided. Embodiments of the penetrable cap of the present invention include, but are not limited to: an annular sealing portion for engaging an inner surface of a container, a substantially rigid portion extending radially inward from the annular sealing portion; a flexible transition portion extending radially inward from the substantially rigid portion; and a penetrable portion extending radially inward from the transition portion for closing the opening defined by the container. Thus, embodiments of the present invention may thus allow the penetrable portion to elastically deform about the transition portion to a generally convex shape so as to exert a radially outward force that may be transmitted by the substantially rigid portion to the annular sealing portion so as to reinforce a fluid-tight seal between the annular sealing portion and the inner surface of the container.

25 Claims, 3 Drawing Sheets

U.S. PATENT DOCUMENTS

| | | | |
|---|---|---|---|
| 3,990,598 A | 11/1976 | Zapp et al. | |
| 4,134,512 A | 1/1979 | Nugent | |
| 4,152,269 A | 5/1979 | Babson | |
| 4,278,437 A | 7/1981 | Haggar | |
| 4,349,035 A | 9/1982 | Thomas et al. | |
| 4,515,752 A | 5/1985 | Miramanda | |
| 4,600,112 A | 7/1986 | Shillington et al. | |
| 4,610,372 A | 9/1986 | Swartzbaugh | |
| 4,693,834 A | 9/1987 | Hossom | |
| 4,714,167 A | 12/1987 | Sandhaus | |
| 4,768,669 A | 9/1988 | Kane et al. | |
| 4,995,521 A | 2/1991 | von Schuckmann | |
| 5,045,081 A | 9/1991 | Dysarz | |
| 5,103,990 A | 4/1992 | Irwin | |
| 5,125,921 A | 6/1992 | Duschek | |
| 5,202,093 A | 4/1993 | Cloyd | |
| 5,230,428 A * | 7/1993 | McShane | 206/363 |
| 5,251,770 A | 10/1993 | Bartley et al. | |
| D341,779 S | 11/1993 | Lewis | |
| 5,297,599 A | 3/1994 | Bucheli | |
| D349,648 S | 8/1994 | Tirrell et al. | |
| 5,425,465 A | 6/1995 | Healy | |
| 5,429,256 A | 7/1995 | Kestenbaum | |
| 5,458,252 A | 10/1995 | Logel | |
| 5,707,589 A | 1/1998 | Fullemann | |
| D414,694 S | 10/1999 | Richter | |
| D445,908 S | 7/2001 | Conway | |
| 6,361,744 B1 | 3/2002 | Levy | |
| 6,367,668 B1 | 4/2002 | Schwanenberg | |
| D457,247 S | 5/2002 | Iheme et al. | |
| 6,405,609 B1 | 6/2002 | Richards et al. | |
| 6,562,300 B2 | 5/2003 | Rosen et al. | |
| 6,702,134 B2 | 3/2004 | Scalese et al. | |
| 6,716,396 B1 | 4/2004 | Anderson et al. | |
| 6,723,289 B2 | 4/2004 | Iheme et al. | |
| 6,752,965 B2 | 6/2004 | Levy | |
| 6,806,094 B2 | 10/2004 | Anderson et al. | |
| 6,893,612 B2 | 5/2005 | Kacian et al. | |
| 2003/0052074 A1 | 3/2003 | Chang et al. | |
| 2004/0067169 A1 | 4/2004 | Krause | |
| 2004/0159579 A1 | 8/2004 | Winckels et al. | |
| 2004/0256348 A1 | 12/2004 | Stevens et al. | |

FOREIGN PATENT DOCUMENTS

| | | | |
|---|---|---|---|
| EP | 1 491 456 | A2 | 12/2004 |
| FR | 699881 | A | 2/1931 |
| JP | 56-118843 | U | 9/1981 |
| WO | WO 95/32128 | A1 | 11/1995 |

* cited by examiner

CONTAINER ASSEMBLY AND PRESSURE-RESPONSIVE PENETRABLE CAP FOR THE SAME

FIELD OF THE INVENTION

The present invention relates generally to penetrable caps for selectively sealing a container containing a fluid (such as a biological fluid specimen). More particularly, the present invention provides a penetrable cap that is capable of elastically deforming in response to a pressure differential between the interior and the exterior of the container such that, as the pressure inside the container is increased, the deformation of the cap may act to increase the sealing force between an annular sealing portion of the penetrable cap and an inner surface of the container.

BACKGROUND OF THE INVENTION

A number of containers and complementary penetrable sealing caps have been developed for sealing and selectively dispensing fluids, such as pharmaceuticals and liquid biological specimens. For example, many conventional containers and caps (such as those produced to package pharmaceuticals meant to be injected via needle and syringe) are penetrable self-sealing caps that extend distally into an aperture defined by a vial or other container body such that the cap may guide a needle and/or syringe towards a penetrable portion of the cap that includes, for example, a self-sealing diaphragm that is designed to elastically return to a closed state after being pierced by a syringe or needle extending therefrom. For example, some conventional containers include self-sealing caps with penetrable portions including pre-defined slits or depressions including edges that are designed to return to a closed position after removal of a syringe or other piercing element that may engage the cap to remove products from the container with which the cap is engaged. Other conventional containers require the use of separate sealing liners in conjunction with the cap in order to completely seal a container with a substantially fluid-tight seal.

Furthermore, other conventional containers and sealing caps (such as those produced to package liquid consumer goods) may also include pressure-responsive diaphragms that are designed to respond to pressure differentials between an interior of the container and the ambient environment (due to, for example, transport in an unpressurized aircraft cargo hold). For example, such conventional pressure-responsive containers and caps are designed to plastically deform in response to the pressure differential so as to bulge proximally from the container interior so as to alert a downstream user of the container that the container has experienced a potential breach due to pressure forces.

Such conventional containers and sealing caps may provide re-sealing capabilities and may also provide easily-identifiable indications that the cap has been plastically deformed and that the container has been irreparably breached by a pressure differential between the interior of the container and the ambient environment. However, such conventional containers and caps are not well-suited for providing an elastic deformation in response to an internal pressure build-up that may augment the sealing capacity of the cap. Instead, the conventional containers described above plastically deform and eventually disengage from a sealing engagement with the container in response to a large pressure differential. Furthermore, conventional containers and sealing caps such as the type described generally above may not be well-suited to transfer forces generated by the elastic deformation of a somewhat flexible penetrable portion of the cap so as to augment sealing engagement between the cap and container.

Thus, there is a need in the art for a container and a complementary pressure-responsive cap may generate lateral sealing forces in response to a pressure differential between the exterior and the interior of the container.

SUMMARY OF THE INVENTION

Embodiments of the present invention satisfy the needs listed above and provide other advantages as described below. Embodiments of the present invention may include a container assembly comprising a container defining an opening therein and a penetrable cap adapted to be capable of cooperating with the container to selectively close the opening. Furthermore, the container may comprise an outer surface and an inner surface accessible via the opening. The penetrable cap may comprise, in some embodiments, an annular sealing portion having a radially-outward surface and a radially-inward surface, wherein the radially-outward surface may be adapted to sealingly engage the inner surface of the container. Furthermore, the radially-inward surface of the annular sealing portion may include a proximal edge and a distal edge, wherein the distal edge is disposed substantially within the container. Furthermore, the penetrable cap may also comprise a substantially rigid portion operably engaged with and extending radially inward from the radially-inward surface of the annular sealing portion. The substantially rigid portion may include a distal end and may be formed from a substantially rigid material so as to be effective in transmitting lateral sealing forces to the annular sealing portion. The penetrable cap may also comprise a transition portion operably engaged with and extending radially inward from the distal end of the substantially rigid portion. The transition portion may, in some embodiments, be configured to be capable of flexing relative to the substantially rigid portion. The penetrable cap may also comprise a penetrable portion operably engaged with and extending radially inward from the transition portion for closing the opening defined by the container. The penetrable portion may be adapted to be easily breached by a pipette, syringe, needle, or other tool or implement. In some embodiments, the penetrable portion may be configured to be capable of elastically deforming about the transition portion towards the proximal edge of the annular sealing portion in response to a positive pressure generated within the container. The elastic deformation of the penetrable portion may further exert a radially outward force that is transmitted by the substantially rigid portion to the radially-outward surface of the annular sealing portion so as to reinforce a seal between the radially-outward surface of the annular sealing portion and the inner surface of the container.

According to some additional embodiments, the container may further comprise a lip portion disposed about a periphery of the opening defined therein. According to some such embodiments, the penetrable cap may further comprise a flange portion operably engaged with and extending radially outward from the proximal edge of the radially-inward surface of the annular sealing portion. Thus, the flange portion may be configured to cooperate with the lip portion of the container to selectively close and more completely seal the opening. In order to secure the penetrable cap to the container, the penetrable cap may also comprise, in some embodiments, an annular restraining portion operably engaged with an extending distally from the flange portion so as to operably engage the outer surface of the container. In some container assembly embodiments of the present invention, the outer surface of the container may define a container screw thread.

Furthermore, the annular restraining portion of the penetrable cap may also comprise a radially-inward surface defining a corresponding cap screw thread configured to cooperate with the container screw thread to engage the annular restraining portion with the outer surface of the container. In some other embodiments, the annular restraining portion of the penetrable cap may also comprise a radially-outward surface defining a plurality of distally extending ridges for traction such that a user may tighten and/or loosen the penetrable cap with respect to the container.

In some embodiments, the penetrable cap may further comprise a sealing bead extending distally from the flange portion about a circumference of the flange portion for ensuring a more fluid-tight engagement between the penetrable cap and the container. The sealing bead may comprise a substantially flexible material such that as the annular restraining portion of the penetrable cap is operably engaged with the outer surface of the container, the sealing bead may deform against the lip portion of the container to form a substantially fluid-tight seal between the flange portion of the penetrable cap and the lip portion of the container.

According to various embodiments of the present invention, the annular sealing portion, the substantially rigid portion, the transition portion, and the penetrable portion may be integrally formed as a substantially unitary penetrable cap. For example, in some embodiments, the annular sealing portion, the substantially rigid portion, the transition portion, and the penetrable portion may be integrally formed as a substantially unitary penetrable cap using manufacturing processes that may include, but are not limited to: injection molding; blow molding; casting; and combinations of such processes. Furthermore, in some embodiments, the annular sealing portion, the substantially rigid portion, the transition portion, and the penetrable portion of the penetrable cap may comprise various polymeric materials including, but not limited to: polyethylene terephthalate (PETE); polyvinyl chloride (PVC); high-density polyethylene (HDPE); low-density polyethylene (LDPE); medium-density polyethylene (MDPE); and combinations of such materials.

Furthermore, in some container assembly embodiments of the present invention, the container may be a substantially cylindrical vial, and the penetrable cap may have a corresponding circular shape for engaging a circular opening defined in a proximal end of the substantially cylindrical vial. Furthermore, according to various container assembly embodiments of the present invention, the container may comprise various polymeric materials including, but not limited to: polyethylene terephthalate (PETE); polyvinyl chloride (PVC); high-density polyethylene (HDPE); low-density polyethylene (LDPE); medium-density polyethylene (MDPE); and combinations of such materials.

Thus the various embodiments of the package assembly of the present invention provide many advantages that may include, but are not limited to: providing a penetrable sealing cap with an elastically-deformable penetrable portion that may generate a lateral sealing force in response to a positive pressure differential inside a container; providing a substantially rigid portion that may more effectively transmit the lateral sealing force to a sealing portion of the penetrable cap as well as serve as a small-volume reservoir for retaining fluids that may remain in container after the penetrable cap has been breached; and providing an integrally-formed, one-piece, pressure-responsive, penetrable sealing cap that is capable of being formed using readily available polymeric materials and low-cost manufacturing techniques.

These advantages, and others that will be evident to those skilled in the art, are provided in the various container assembly and penetrable cap embodiments of the present invention.

BRIEF DESCRIPTION OF THE DRAWINGS

Figure 1:
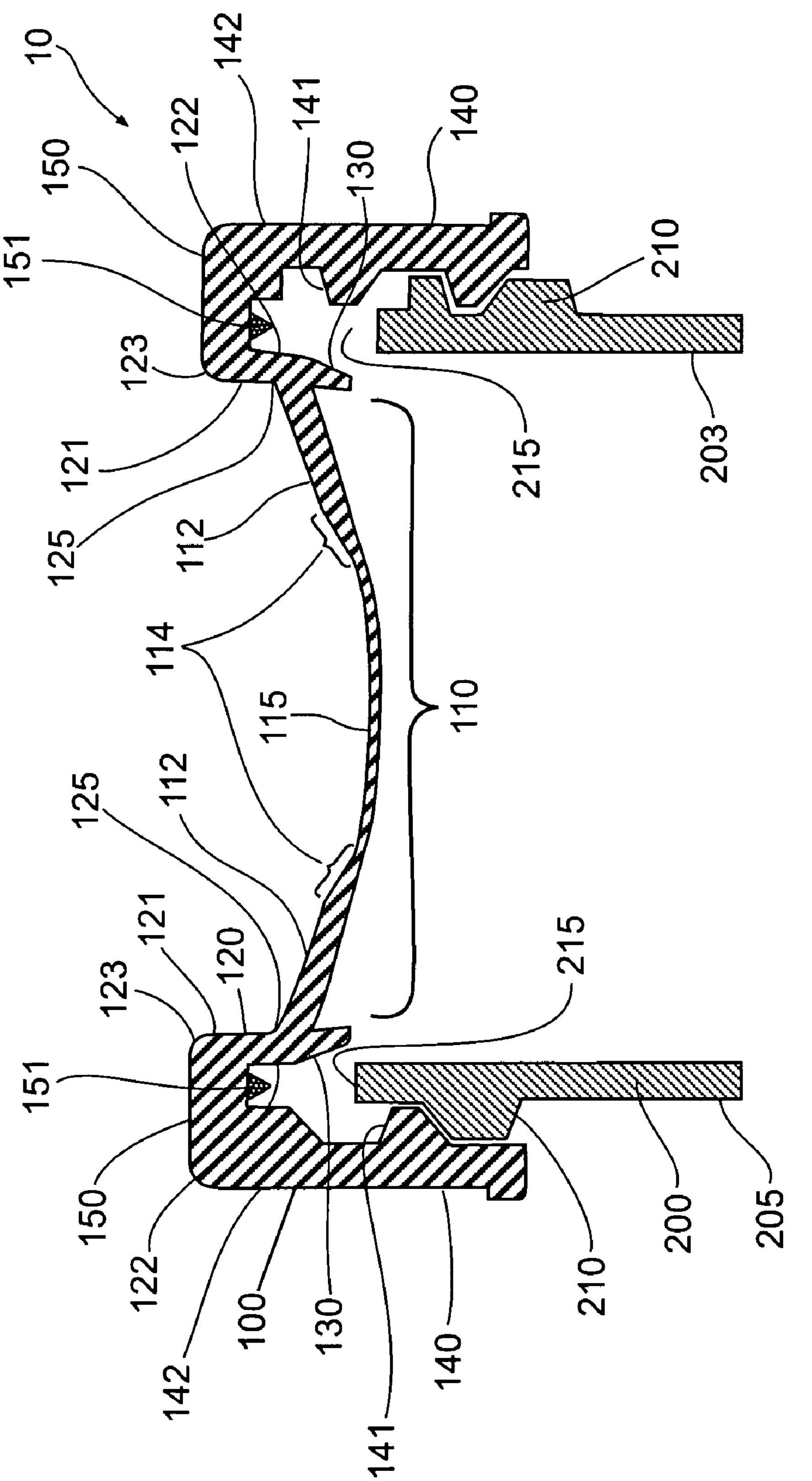
Figure 2:
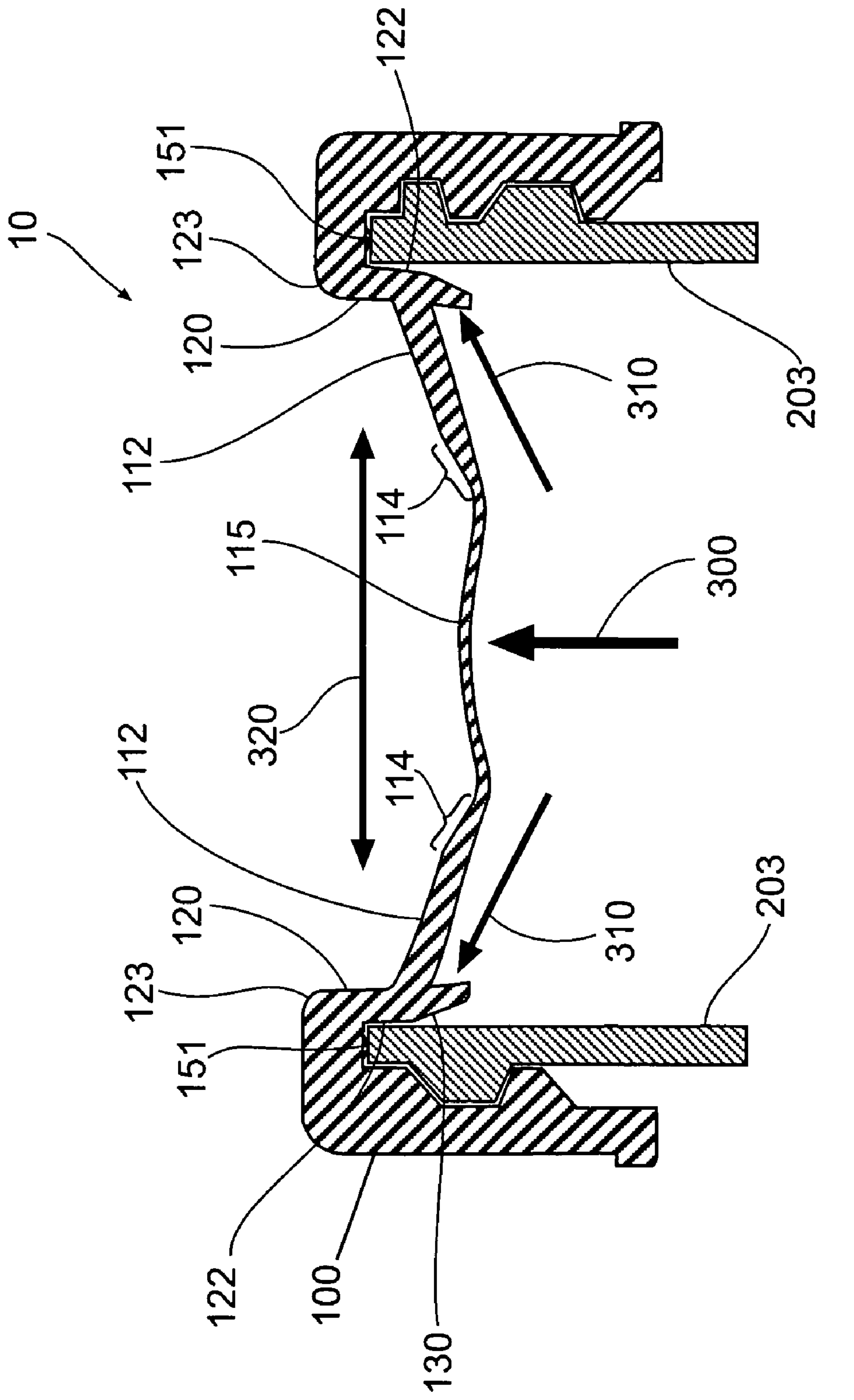
Figure 3:
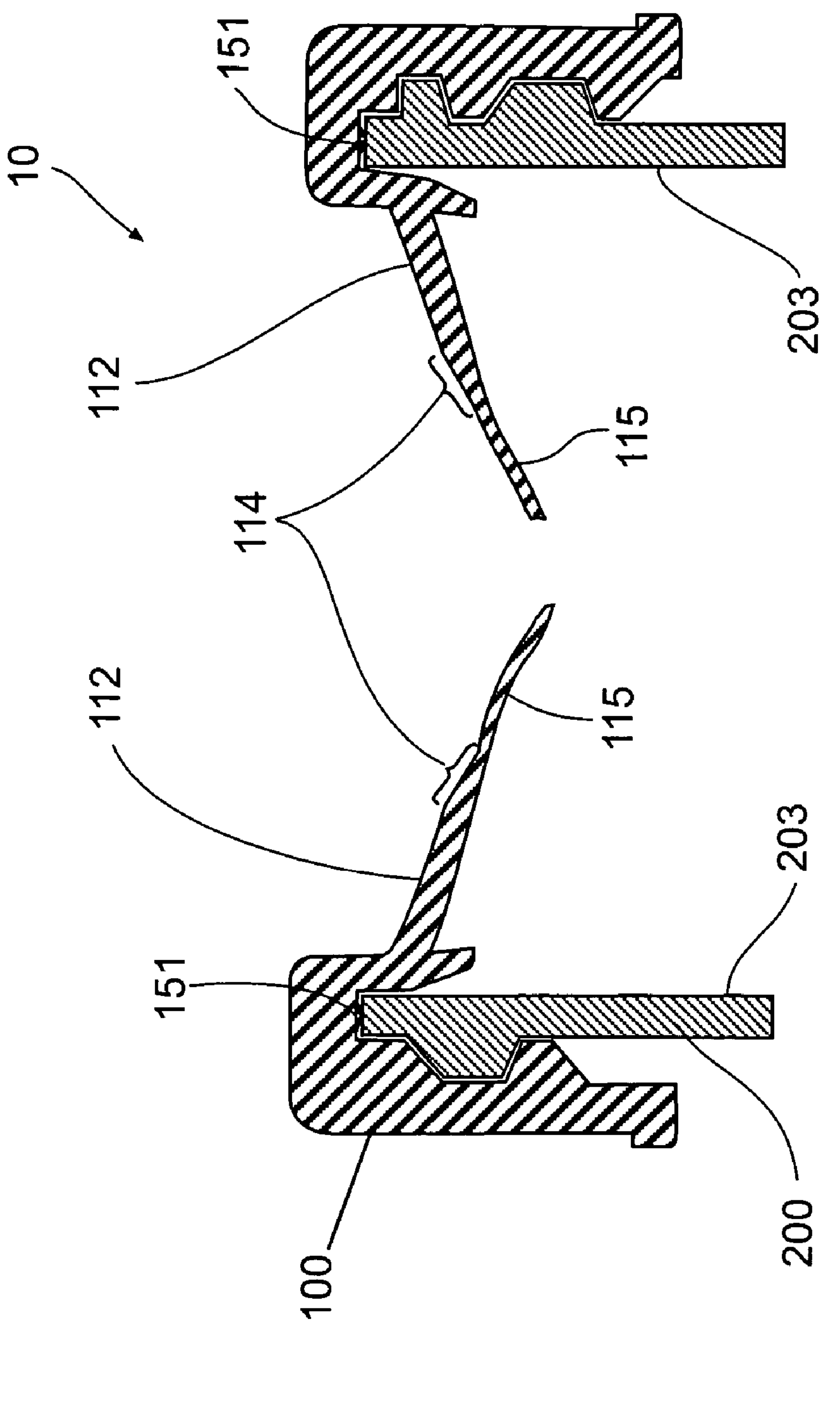

Having thus described the invention in general terms, reference will now be made to the accompanying drawings, which are not necessarily drawn to scale, and wherein:

FIG. 1 shows a cross-sectional side view of a container assembly according to one embodiment of the present invention wherein the penetrable cap is positioned adjacent to the container prior to sealing the opening defined in the container;

FIG. 2 shows a cross-sectional side view of a container assembly according to one embodiment of the present invention wherein the penetrable cap is operably engaged with the container and wherein the penetrable portion is deformed proximally in response to a positive pressure within the container; and FIG. 3 shows a cross-sectional side view of a container assembly according to one embodiment of the present invention wherein the penetrable cap is operably engaged with the container and wherein the penetrable portion of the penetrable cap is breached such that the contents of the container may be removed via pipette, syringe, or other methods.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

While the embodiments of the present invention are described below in the context of a container assembly 10 and penetrable cap 100 for containing fluids in a substantially fluid-tight container assembly 10, it should be understood that the container assembly 10 and penetrable cap 100 embodiments of the present invention may also serve as a closable and selectively penetrable container assembly 10 for containing and sealing particulates or other solid or semi-solid materials from the ingress of fluids including gases and/or liquids. For example, in some embodiments, the container assembly 10 of the present invention may be used to contain solid and/or semi-solid materials in a pressurized substantially-pure gas (such as substantially pure nitrogen gas) environment such that the internal pressure of the container 200 may act to elastically deform the penetrable portion 115 of the penetrable cap 100 to exert a lateral sealing force 320 on an inner surface 203 of the container 200.

FIG. 1 shows a cross-sectional side view of a container assembly 10 according to one embodiment of the present invention. FIG. 1 generally shows a container 200 defining an opening therein, wherein the container 200 includes an outer surface 205 and an inner surface 203 that is generally accessible via the opening. FIG. 1 also shows a penetrable cap 100 positioned adjacent the container 200 for selectively closing the opening defined therein but not yet fully engaged with the container 200 as described more fully below and shown generally in FIG. 2. The penetrable cap 100 of the present invention may be configured to be capable of cooperating with the container 200 to selectively close the opening. According to some exemplary embodiments of the present invention, the container 200 may be formed as a substantially cylindrical vial having a substantially circular opening at one end thereof. According to such embodiments, the penetrable cap 100 may be formed in a substantially circular shape so as to be capable of operably engaging the inner and outer surfaces 203, 205 of the container 200 near the opening defined therein so as to effectively close and/or seal the opening as described in further detail below.

The container 200 may include, but is not limited to a specialized container designed to receive biological samples. In some embodiments, the container 200 may be a substantially cylindrical vial, and the penetrable cap 100 may have a corresponding circular shape for engaging a circular opening defined in a proximal end of the substantially cylindrical vial. Furthermore, according to various embodiments of the present invention, the container 200 may comprise various polymeric materials including, but not limited to: polyethylene terephthalate (PETE); polyvinyl chloride (PVC); high-density polyethylene (HDPE); low-density polyethylene (LDPE); medium-density polyethylene (MDPE); and combinations of such materials.

According to some exemplary embodiments, the penetrable cap 100 may comprise an annular sealing portion 120 extending into the container 200 and having a radially-outward surface 122 and a radially-inward surface 121. Furthermore, the radially-outward surface 122 may be configured to sealingly engage the inner surface of the container 203 in a "plug-type" interference fit. For example, according to some embodiments, the radially-outward surface 122 of the annular sealing portion 120 may be formed with a slight angle relative to the inner surface 203 of the container 200 such that the annular sealing portion 120 sealingly engages the inner surface 203 of the container 200 in a "plug-type" or "stopper" interference fit as shown generally in FIG. 2 (showing the penetrable cap 100 in sealing engagement with the container 200 so as to close the opening defined therein. Furthermore, the radially outward surface 122 of the annular sealing portion 120 may also define an angled or beveled lead-in 130 (or "in-feed") for guiding the annular sealing portion 120 into a seating position substantially in the center of the opening defined in the container 200 such that the penetrable cap 100 may be fully centered and properly sealed when the penetrable cap 100 is operably engaged with the container 200 (as shown generally in FIG. 2).

Furthermore, the radially-inward surface 121 of the annular sealing portion 120 may include a proximal edge 123 and a distal edge 125 wherein the distal edge 125 may be disposed substantially within the container 200 such that the substantially rigid portion 112 and the penetrable portion 115 supported thereby (see FIGS. 1 and 2) may be supported generally within the container 200 and distal to the region of sealing engagement between the radially-outward surface 122 of the annular sealing portion 120 and the inner surface 203 of the container 200. Thus the radially-inward surface 121 of the annular sealing portion 120 (in conjunction with the substantially rigid portion 112 described in further detail below) may cooperate to guide a piercing tool (such as a pipette, syringe, needle, and/or other piercing element) generally towards the penetrable portion 115 of the penetrable cap 100.

As shown in FIGS. 1-3, various embodiments of the penetrable cap 100 of the present invention may also comprise a substantially rigid portion 112 operably engaged with and extending radially inward from the radially-inward surface 121 of the annular sealing portion 120. As described in further detail below, the substantially rigid portion 112 may be formed from a substantially rigid material so as to be capable of transferring a radially-outward force 320 (see FIG. 2, generally), generated by the elastic deformation of the penetrable portion 115 of the penetrable cap 100, to the annular sealing portion 120 such that the radially-outward surface 122 of the annular sealing portion 120 is urged into sealing engagement with the inner surface 203 of the container 200. According to some embodiments, the substantial rigidity of the substantially rigid portion 112 may be achieved by forming the substantially rigid portion 112 from generally rigid polymeric materials (such as PVC or high molecular-weight polymers that will be appreciated by one skilled in the art). According to other embodiments, wherein the various components of the penetrable cap 100 (including, for example, the annular sealing portion 120, the substantially rigid portion 112, the transition portion 114, and the penetrable portion 115) are formed generally of the same material components, the general overall thickness of the substantially rigid portion 112 (in radial cross-section, as shown generally in FIG. 1) may be increased relative to the adjacent transition portion 114 and relative to the central penetrable portion 115 in order to impart substantial rigidity to the substantially rigid portion 112. For example, in some embodiments, the substantially rigid portion 112 may be formed with a thickness having a range substantially between about 0.035 inches and about 0.046 inches.

The relatively rigid structure of the substantially rigid portion 112, in some exemplary embodiments, may also serve as a reservoir for fluids that may remain in the container 200 after the penetrable cap 100 has been pierced such that the penetrable portion 115 has been removed (as shown generally in FIG. 3, for example). Thus, even if the container 200 were to fall to its side (with its outer surface 205 pointing generally downward, for example) at least some portion of a liquid remaining in the container 200 may be suspended between the substantially rigid portion 112 and the inner surface 203 of the container 200. This feature and advantage of the container assembly 10 of the present invention may be very important in some cases. For example, in embodiments wherein the container assembly 10 and/or the container 200 is used to contain a biological sample for a drug test and/or evidentiary purposes in a criminal prosecution, the substantially rigid portion 112 may prevent the complete loss of such a sample in the event that the container 200 is accidentally dropped after the penetrable portion 115 is breached (see FIG. 3, for example) but before a suitable aliquot of the fluid sample has been transferred to an analysis device and/or to an aliquot container for laboratory and/or evidentiary use.

According to some embodiments of the present invention, as shown generally in FIG. 1, the penetrable cap 100 may further comprise a transition portion 114 operably engaged with and extending radially inward from the distal end of the substantially rigid portion 112. The transition portion 114 may, in some embodiments, be configured to be capable of flexing relative to the substantially rigid portion 112. In some embodiments, the transition portion 114 may flex relative to the substantially rigid portion 112 such that the angle of the transition portion 114, as described in further detail below, relative to the substantially rigid portion 112 may change in response to changes in pressure (such as the development of a positive pressure 300) within the container 200. Furthermore, in some embodiments, the transition portion 114 may be provided with a material thickness that gradually decreases in the radially-inward direction from a first dimension at a junction with the substantially rigid portion 112 to a second, smaller dimension at a junction with the penetrable portion 115. For example, in some embodiments, the transition portion 114 may be formed with a maximum thickness having a range substantially between about 0.035 inches and about 0.046 inches. Furthermore, in some embodiments, the transition portion 114 may be formed with a minimum thickness substantially similar to the thickness of the penetrable portion 115 which, in some embodiments, may have a thickness ranging substantially between about 0.014 inches and about 0.018 inches.

In other embodiments, the transition portion 114 may also be defined as a "notch" or other area of reduced material thickness (relative to the adjacent substantially rigid portion 112 and penetrable portion 115, for example) such that the transition portion 114 may serve as a hinged perimeter about which the penetrable portion 115 may deform in response to a positive pressure 300 developed within the container 200. Thus, as described generally above, the penetrable portion 115 of the penetrable cap 100 may generally deform about the perimeter defined by the transition portion 114 when a positive pressure 300 is exerted on the penetrable portion 115 (as shown generally in FIG. 2). In other embodiments, the transition portion 114 of the penetrable cap may be formed from generally flexible and/or "soft" polymeric materials (such as LDPE or other generally low molecular-weight polymers that will be appreciated by one skilled in the art).

Furthermore, as shown in FIGS. 1 and 2, the penetrable cap 100 may also comprise a penetrable portion 115 operably engaged with and extending radially inward from the transition portion 114 so as to completely close the opening defined by the container 200. In order to exhibit generally elastic behavior in response to a positive pressure force 300, as shown in FIG. 2, and to ensure that piercing tools (such as, for example, pipettes, syringes, needles, and/or other piercing implements) may be capable of penetrating the penetrable portion 115, the penetrable portion 115 may be formed from generally mid-weight polymeric materials (such as MDPE or other medium molecular-weight polymers that will be appreciated by one skilled in the art). In other embodiments, wherein the various components of the penetrable cap 100 (including, for example, the annular sealing portion 120, the substantially rigid portion 112, the transition portion 114, and the penetrable portion 115) are formed generally of the same material components, the penetrable portion 115 may be formed with a material thickness equal to and/or less than the thickness of the transition portion 114 (and therefore less than a thickness of the substantially rigid portion 112) so as to respond elastically to a positive pressure 300 by generating a radially-outward force 320. The penetrable portion 115 may be formed with a thickness having a range substantially between about 0.014 inches and about 0.018 inches.

In operation, and as shown generally in FIG. 2, some exemplary embodiments of the penetrable portion 115 may elastically deform about the transition portion 114 towards the proximal edge 123 of the annular sealing portion 120 to assume a convex shape (see FIG. 2, for example) in response to a positive pressure 300 generated within the container 200 such that the penetrable portion 115 may exert a radially outward force 320 that is transmitted by the substantially rigid portion 112 (as an angular force component 310, for example) to the radially-outward surface 122 of the annular sealing portion 120 so as to reinforce a seal between the radially-outward surface 122 of the annular sealing portion 120 and the inner surface 203 of the container 200.

In other embodiments, as shown generally in FIG. 1, the container 200 may further comprise a lip portion 215 disposed about a periphery of the opening defined therein. Furthermore, the penetrable cap 100 may further comprise a flange portion 150 operably engaged with and extending radially outward from the proximal edge 123 of the radially-inward surface 121 of the annular sealing portion 120. Thus, as shown in FIG. 2 (showing the penetrable cap 100 operably engaged with the container portion 200, for example) the flange portion 150 may be configured to cooperate with the lip portion 215 of the container 200 to selectively close the opening defined therein. The flange portion 150 may further prevent the penetrable cap 100 from being seated distally in the container 200.

Also, as shown in FIG. 1, the penetrable cap 100 may also further comprise an annular restraining portion 140 operably engaged with and extending distally from the flange portion 150 so as to operably engage the outer surface 205 of the container 200. Thus, as shown in FIG. 2, the annular sealing portion 120 and the annular restraining portion 140 may cooperate to "sandwich" the wall of the container 200 when the penetrable cap 100 is operably engaged with the container 200. In some embodiments, the outer surface 205 of the container 200 may define a container screw thread 210 and the annular restraining portion 140 of the penetrable cap 100 may comprises a radially-inward surface defining a complementary cap screw thread 141 configured to cooperate with the container screw thread 210 so as to operably engage the annular restraining portion 140 with the outer surface 205 of the container 200. In some alternative embodiments, the radially-inward surface of the annular restraining portion 140 may comprise one or more generally deformable cap ridges that may operably engage complementary container ridges that may be defined by the outer surface 205 of the container 200. Thus, in various alternative embodiments of the container assembly 10 of the present invention, the penetrable cap 100 may be "snapped" on to the container 200 and/or "screwed" on to the container 200 (via the interaction of complementary sets of screw threads (141, 210)). Furthermore, according to various embodiments of the container assembly 10 and penetrable cap 100 of the present invention, the annular restraining portion 140 of the penetrable cap 100 may comprise a radially-outward surface 142 defining a plurality of ridges or other textured features (such as, for example, knurling) for traction such that a user may rotate the penetrable cap 100 relative to the container body 200 so as to operably engage (and effectively seal, as shown in FIG. 2, for example) the penetrable cap 100 with the container 200.

In order to augment the sealing capability of the penetrable cap 100 and to prevent the leakage of fluids at the interfaces between the penetrable cap 100 and the various surfaces 203, 205 and lip portion 215 of the penetrable cap 100, some alternative embodiments of the penetrable cap 100 (shown generally in FIG. 1) may further comprise a sealing bead 151 protruding from the flange portion 150 about a circumference of the flange portion 150. In some embodiments, the sealing bead 150 may comprise a substantially flexible material (such as, for example, a rubber and/or a generally low molecular-weight polymer) such that as the annular restraining portion 140 of the penetrable cap 100 is operably engaged with the outer surface 203 of the container (via the interaction of complementary sets of screw threads 141, 210, for example), the sealing bead 151 may deform against the lip portion 215 of the container 200 to form a substantially fluid-tight seal between the flange portion 150 of the penetrable cap 100 and the lip portion 215 of the container 200.

As discussed generally above, in some exemplary embodiments, various components of the penetrable cap 100 (such as, for example, the annular sealing portion 120, the substantially rigid portion 112, the transition portion 114, and the penetrable portion 115) may be integrally formed as a substantially unitary penetrable cap 100. In some embodiments, the flange portion 150, annular restraining portion 140, and sealing bead 151 may also be integrally formed with other components of the penetrable cap 100. In some embodiments wherein the various components of the penetrable cap 100 are integrally formed as a substantially unitary penetrable cap 100 the penetrable cap 100 may be formed using various types of relatively low-cost manufacturing techniques which may include, but are not limited to: injection molding; blow molding; casting and combinations of such processes. In addition, the container 200, the annular sealing portion 120, the substantially rigid portion 112, the transition portion 114, the penetrable portion 115, the flange portion 150, annular restraining portion 140, and the sealing bead 151 may comprise various materials that may include, but are not limited to: polyethylene terephthalate (PETE); polyvinyl chloride (PVC); high-density polyethylene (HDPE); low-density polyethylene (LDPE); medium-density polyethylene material blends; and combinations of such materials.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A container assembly comprising:

a container defining an opening therein, the container comprising an outer surface and an inner surface accessible via the opening; and a penetrable cap configured to be capable of cooperating with the container to selectively close the opening, the penetrable cap comprising:

an annular sealing portion extending into the container and having a radially-outward surface and a radially-inward surface, the radially-outward surface configured to sealingly engage, via abutting contact, the inner surface of the container, the radially-inward surface having a proximal edge and a distal edge, the distal edge being disposed substantially within the container;

an annular substantially rigid portion operably engaged with and extending radially inward from the radially-inward surface of the annular sealing portion at a selected angle relative to the radially-inward surface of the annular sealing portion, the annular substantially rigid portion having a distal end;

an annular transition portion operably engaged with and extending radially inward from the distal end of the annular substantially rigid portion, the transition portion being capable of flexing relative to the annular substantially rigid portion;

a penetrable portion operably engaged with and extending radially inward from the annular transition portion, the penetrable portion being capable of elastically deforming about the annular transition portion towards the proximal edge of the annular sealing portion in response to a positive pressure generated within the container while the annular substantially rigid portion remains oriented at the selected angle relative to the radially-inward surface of the annular sealing portion such that the penetrable portion exerts a radially outward force that is transmitted by the annular substantially rigid portion to the radially-outward surface of the annular sealing portion so as to reinforce a seal between the radially-outward surface of the annular sealing portion and the inner surface of the container, and the penetrable portion having a thickness less than the annular substantially rigid portion to facilitate piercing by a piercing tool.

2. The container assembly according to claim 1, wherein the container further comprises a lip portion disposed about a periphery of the opening defined therein and wherein the penetrable cap further comprises a flange portion operably engaged with and extending radially outward from the proximal edge of the radially-inward surface of the annular sealing portion, the flange portion configured to cooperate with the lip portion of the container to selectively close the opening.

3. The container assembly according to claim 2, wherein the penetrable cap further comprises an annular restraining portion operably engaged with and extending distally from the flange portion so as to operably engage the outer surface of the container.

4. The container assembly according to claim 3, wherein the outer surface of the container defines a container screw thread and wherein the annular restraining portion comprises a cap screw thread configured to cooperate with the container screw thread so as to operably engage the annular restraining portion with the outer surface of the container.

5. The container assembly according to claim 3, wherein the annular restraining portion comprises a radially-outward surface defining a plurality of ridges for traction.

6. The container assembly according to claim 4, wherein the penetrable cap further comprises a sealing bead protruding from the flange portion about a circumference of the flange portion, the sealing bead comprising a substantially deformable material such that as the annular restraining portion of the penetrable cap is operably engaged with the outer surface of the container, the sealing bead deforms against the lip portion of the container to form a substantially fluid-tight seal between the flange portion of the penetrable cap and the lip portion of the container.

7. The container assembly according to claim 1, wherein the annular sealing portion, the annular substantially rigid portion, the annular transition portion, and the penetrable portion are integrally formed as a substantially unitary penetrable cap.

8. The container assembly according to claim 7, wherein the annular sealing portion, the annular substantially rigid portion, the annular transition portion, and the penetrable portion are integrally formed as a substantially unitary penetrable cap using a process selected from the group consisting of:

injection molding;
blow molding;
casting; and
combinations thereof.

9. The container assembly according to claim 1, wherein the annular sealing portion, the annular substantially rigid portion, the annular transition portion, and the penetrable portion of the penetrable cap comprise materials selected from the group consisting of:

polyethylene terephthalate;
polyvinyl chloride;
high-density polyethylene;
low-density polyethylene; and
combinations thereof.

10. The container assembly according to claim 1, wherein the container is a substantially cylindrical vial.

11. The container assembly according to claim 1, wherein the container comprises materials selected from the group consisting of:

polyethylene terephthalate;
polyvinyl chloride;
high-density polyethylene;
low-density polyethylene;
medium-density polyethylene;
glass; and
combinations thereof.

12. A penetrable cap adapted to be capable of cooperating with a container to selectively close an opening defined therein, the penetrable cap comprising:

an annular sealing portion extending into the container and having a radially-outward surface and a radially-inward surface, the radially-outward surface adapted to sealingly engage, via abutting contact, an inner surface of the container, the radially-inward surface having a proximal edge and a distal edge, the distal edge being disposed substantially within the container;

an annular substantially rigid portion operably engaged with and extending radially inward from the radially-inward surface of the annular sealing portion at a selected angle relative to the radially-inward surface of the annular sealing portion, the annular substantially rigid portion having a distal end;

an annular transition portion operably engaged with and extending radially inward from the distal end of the annular substantially rigid portion, the annular transition portion being capable of flexing relative to the annular substantially rigid portion;

a penetrable portion operably engaged with and extending radially inward from the annular transition portion, the penetrable portion being capable of elastically deforming about the annular transition portion towards the proximal edge of the annular sealing portion in response to a positive pressure generated within the container while the annular substantially rigid portion remains oriented at the selected angle relative to the radially-inward surface of the annular sealing portion such that the penetrable portion exerts a radially outward force that is transmitted by the annular substantially rigid portion to the radially-outward surface of the annular sealing portion so as to reinforce a seal between the radially-outward surface of the annular sealing portion and the inner surface of the container, and the penetrable portion having a thickness less than the annular rigid portion to facilitate piercing by a piercing tool.

13. The penetrable cap according to claim 12, further comprising a flange portion operably engaged with and extending radially outward from the proximal edge of the radially-inward surface of the annular sealing portion, the flange portion adapted to cooperate with a lip portion of the container disposed about a periphery of the opening defined therein.

14. The penetrable cap according to claim 13, further comprising an annular restraining portion operably engaged with and extending distally from the flange portion so as to operably engage an outer surface of the container.

15. The penetrable cap according to claim 14, wherein the annular restraining portion comprises a radially-inward surface defining a cap screw thread adapted to cooperate with a corresponding container screw thread defined in the outer surface of the container so as to operably engage the annular restraining portion with the outer surface of the container.

16. The penetrable cap according to claim 14, wherein the annular restraining portion comprises a radially-outward surface defining a plurality of ridges for traction.

17. The penetrable cap according to claim 15, further comprising a sealing bead protruding from the flange portion about a circumference of the flange portion, the sealing bead comprising a substantially deformable material such that as the annular restraining portion is operably engaged with the outer surface of the container, the sealing bead deforms against the lip portion of the container to form a substantially fluid-tight seal between the flange portion and the lip portion of the container.

18. The penetrable cap according to claim 12, wherein the annular sealing portion, the annular substantially rigid portion, the annular transition portion, and the penetrable portion are integrally formed as a substantially unitary assembly.

19. The penetrable cap according to claim 18, wherein the annular sealing portion, the annular substantially rigid portion, the annular transition portion, and the penetrable portion are integrally formed as a substantially unitary assembly using a process selected from the group consisting of:

injection molding;
blow molding;
casting; and
combinations thereof.

20. The penetrable cap according to claim 12, wherein the annular sealing portion, the annular substantially rigid portion, the annular transition portion, and the penetrable portion comprise materials selected from the group consisting of:

polyethylene terephthalate;
polyvinyl chloride;
high-density polyethylene;
low-density polyethylene;
medium-density polyethylene; and
combinations thereof.

21. The container assembly according to claim 1, wherein the penetrable portion has a thickness ranging substantially between about 0.014 inches and about 0.018 inches.

22. The penetrable cap according to claim 12, wherein the penetrable portion has a thickness ranging substantially between about 0.014 inches and about 0.018 inches.

23. The penetrable cap according to claim 12, wherein the penetrable portion has a substantially constant thickness along its entire length.

24. The penetrable cap according to claim 12, wherein a thickness of the annular rigid portion and the annular transition portion gradually decreases from the annular sealing portion to the penetrable portion.

25. The penetrable cap according to claim 12, wherein the penetrable portion has a thickness less than the annular transition portion.

* * * * *

UNITED STATES PATENT AND TRADEMARK OFFICE

CERTIFICATE OF CORRECTION

PATENT NO. : 8,177,084 B2
APPLICATION NO. : 11/353482
DATED : May 15, 2012
INVENTOR(S) :Fox et al.

It is certified that error appears in the above-identified patent and that said Letters Patent is hereby corrected as shown below:

Column 11,
Line 44, "annular rigid portion" should read --annular substantially rigid portion--.

Signed and Sealed this
Twenty-sixth Day of February, 2013

Teresa Stanek Rea
*Acting Director of the United States Patent and Trademark Office*